(12) United States Patent
Hansen

(10) Patent No.: US 12,232,998 B2
(45) Date of Patent: Feb. 25, 2025

(54) APPLICATION OF A STOMAL SENSOR PATCH

(71) Applicant: Coloplast A/S, Humlebaek (DK)

(72) Inventor: Jais Ask Hansen, Jaegerspris (DK)

(73) Assignee: Coloplast A/S, Humlebaek (DK)

( * ) Notice: Subject to any disclaimer, the term of this patent is extended or adjusted under 35 U.S.C. 154(b) by 640 days.

(21) Appl. No.: 17/424,892

(22) PCT Filed: Jan. 30, 2020

(86) PCT No.: PCT/DK2020/050026
§ 371 (c)(1),
(2) Date: Jul. 22, 2021

(87) PCT Pub. No.: WO2020/156624
PCT Pub. Date: Aug. 6, 2020

(65) Prior Publication Data
US 2022/0079802 A1 Mar. 17, 2022

(30) Foreign Application Priority Data
Jan. 31, 2019 (DK) .......................... PA 2019 70069

(51) Int. Cl.
*A61F 5/44* (2006.01)
*A61F 5/443* (2006.01)
(Continued)

(52) U.S. Cl.
CPC ............ *A61F 5/4404* (2013.01); *A61F 5/443* (2013.01); *G01N 27/045* (2013.01); *G01N 27/228* (2013.01)

(58) Field of Classification Search
CPC ........ A61F 5/4404; A61F 5/443; A61F 5/445; G01N 27/045; G01N 27/228
See application file for complete search history.

(56) References Cited

U.S. PATENT DOCUMENTS

| | | | |
|---|---|---|---|
| 2,327,514 | A | 8/1943 | Fenwick |
| 2,542,233 | A | 2/1951 | Carroll |

(Continued)

FOREIGN PATENT DOCUMENTS

| | | |
|---|---|---|
| AU | 2007342523 B2 | 7/2011 |
| CA | 2540756 C | 1/2008 |

(Continued)

*Primary Examiner* — Guy K Townsend
(74) *Attorney, Agent, or Firm* — Coloplast Corp., Coloplast A/S; Nick Baumann

(57) ABSTRACT

Disclosed is a method for evaluating attachment of a sensor patch to a base plate for an ostomy appliance, wherein the base plate (4) comprises: at least a first layer of an adhesive material (200) adapted for attachment of the base plate to the skin surface of a user; a backing layer (208) comprising a film material and having a distal surface and a proximal surface; and a centre portion surrounding a stoma-receiving opening (18) extending through the base plate, the sensor patch being adapted for attachment to the first layer of the base plate, and wherein the sensor patch comprises: a sensor assembly comprising a plurality of electrodes including a first electrode and a second electrode for forming a first sensor, the method comprising: measuring one or more characteristic quantities; and determining whether the one or more characteristic quantities satisfies one or more attachment criteria.

23 Claims, 8 Drawing Sheets

(51) Int. Cl.
*G01N 27/04* (2006.01)
*G01N 27/22* (2006.01)

(56) References Cited

U.S. PATENT DOCUMENTS

| | | |
|---|---|---|
| 2,544,579 A | 3/1951 | Ardner |
| 3,214,502 A | 10/1965 | Schaar |
| 3,808,354 A | 4/1974 | Feezor et al. |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,147,343 A | 9/1992 | Kellenberger |
| 5,237,995 A | 8/1993 | Cano |
| 5,318,543 A | 6/1994 | Ross et al. |
| 5,322,797 A | 6/1994 | Mallow et al. |
| 5,358,488 A | 10/1994 | Suriyapa |
| 5,486,158 A | 1/1996 | Samuelsen |
| 5,519,644 A | 5/1996 | Benton |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,714,225 A | 2/1998 | Hansen et al. |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,846,558 A | 12/1998 | Nielsen et al. |
| 5,876,855 A | 3/1999 | Wong et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,078,261 A | 6/2000 | Davsko |
| 6,093,276 A | 7/2000 | Leise, Jr. et al. |
| 6,101,867 A | 8/2000 | Cavestri |
| 6,103,033 A | 8/2000 | Say et al. |
| 6,135,986 A | 10/2000 | Leisner et al. |
| 6,171,289 B1 * | 1/2001 | Millot .......... A61F 5/443 |
| | | 604/336 |
| 6,206,864 B1 | 3/2001 | Kavanagh et al. |
| 6,241,704 B1 | 6/2001 | Peterson et al. |
| 6,270,445 B1 | 8/2001 | Dean, Jr. et al. |
| 6,407,308 B1 | 6/2002 | Roe et al. |
| 6,433,244 B1 | 8/2002 | Roe et al. |
| 6,433,695 B1 | 8/2002 | Kai et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,677,859 B1 | 1/2004 | Bensen |
| 6,764,474 B2 | 7/2004 | Nielsen et al. |
| 6,774,800 B2 | 8/2004 | Friedman et al. |
| 7,014,816 B2 | 3/2006 | Miller et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,326,051 B1 | 12/2012 | Hobbs |
| 8,343,437 B2 | 1/2013 | Patel |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,439,883 B1 | 5/2013 | Johnsen |
| 8,449,471 B2 | 5/2013 | Tran |
| 8,500,718 B2 | 8/2013 | Locke et al. |
| 8,507,081 B2 | 8/2013 | Strobech et al. |
| 8,632,492 B2 | 1/2014 | Delegge |
| 8,680,991 B2 | 3/2014 | Tran |
| 8,684,982 B2 | 4/2014 | Nguyen-Demary et al. |
| 8,707,766 B2 | 4/2014 | Harris et al. |
| 8,740,865 B2 | 6/2014 | Krystek et al. |
| 8,795,257 B2 | 8/2014 | Coulthard et al. |
| 8,821,463 B2 | 9/2014 | Grum-Schwensen |
| 8,821,464 B2 | 9/2014 | Hanuka et al. |
| 8,975,465 B2 | 3/2015 | Hong et al. |
| 8,978,452 B2 | 3/2015 | Johnson et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,506,886 B1 | 11/2016 | Woodbury et al. |
| 9,566,383 B2 | 2/2017 | Yodfat et al. |
| 9,629,964 B2 | 4/2017 | Wuepper |
| 9,649,230 B1 | 5/2017 | Li |
| 9,675,267 B2 | 6/2017 | Laakkonen et al. |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| 10,022,277 B2 | 7/2018 | Heil et al. |
| D826,740 S | 8/2018 | Stevens et al. |
| 10,426,342 B2 | 10/2019 | Hresko et al. |
| 10,500,084 B2 * | 12/2019 | Hansen .......... A61F 5/443 |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 * | 12/2020 | Hansen .......... A61F 5/443 |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,219,436 B2 | 1/2022 | Mayberg |
| 11,238,133 B1 | 2/2022 | Brewer et al. |
| 11,306,224 B2 | 4/2022 | Chatterjee et al. |
| 11,406,525 B2 | 8/2022 | Seres et al. |
| 11,471,318 B2 | 10/2022 | Hansen et al. |
| 11,547,595 B2 * | 1/2023 | Hansen .......... A61F 5/4404 |
| 11,589,811 B2 * | 2/2023 | Hansen .......... A61B 5/7455 |
| 11,612,509 B2 * | 3/2023 | Hansen .......... G01N 27/20 |
| | | 604/344 |
| 11,612,512 B2 * | 3/2023 | Hansen .......... A61B 5/4851 |
| | | 604/332 |
| 11,622,719 B2 * | 4/2023 | Hansen .......... A61F 5/443 |
| | | 600/301 |
| 11,701,248 B2 * | 7/2023 | Hansen .......... A61F 5/445 |
| | | 604/318 |
| 11,903,728 B2 | 2/2024 | Svanegaard et al. |
| 11,918,506 B2 * | 3/2024 | Hansen .......... A61F 5/445 |
| 12,064,369 B2 | 8/2024 | Hansen et al. |

(56) References Cited

U.S. PATENT DOCUMENTS

| | | |
|---|---|---|
| 2001/0041920 A1 | 11/2001 | Starkweather et al. |
| 2001/0051787 A1 | 12/2001 | Haller et al. |
| 2002/0013613 A1 | 1/2002 | Haller et al. |
| 2002/0019615 A1 | 2/2002 | Roe et al. |
| 2002/0109621 A1 | 8/2002 | Khair et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0038325 A1 | 2/2005 | Moll |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0256545 A1 | 11/2005 | Koh et al. |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2007/0203407 A1* | 8/2007 | Hoss ................ A61B 5/01 600/347 |
| 2007/0204691 A1 | 9/2007 | Bogner et al. |
| 2008/0004580 A1 | 1/2008 | Mullejans et al. |
| 2008/0038536 A1 | 2/2008 | Strobech et al. |
| 2008/0041792 A1 | 2/2008 | Crnkovich et al. |
| 2008/0058740 A1 | 3/2008 | Sullivan et al. |
| 2008/0061965 A1 | 3/2008 | Kuhns et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0255808 A1* | 10/2008 | Hayter ............... A61B 5/6843 708/300 |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1 | 12/2008 | Freedman |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0234916 A1 | 9/2009 | Cosentino et al. |
| 2009/0247970 A1 | 10/2009 | Keleny et al. |
| 2009/0264957 A1 | 10/2009 | Giftakis et al. |
| 2010/0010460 A1 | 1/2010 | Butler |
| 2010/0030167 A1 | 2/2010 | Thirstrup et al. |
| 2010/0072271 A1 | 3/2010 | Thorstensson |
| 2010/0106220 A1 | 4/2010 | Ecker et al. |
| 2010/0114047 A1 | 5/2010 | Song et al. |
| 2010/0191201 A1 | 7/2010 | Bach et al. |
| 2010/0271212 A1 | 10/2010 | Page |
| 2010/0311167 A1 | 12/2010 | Wood et al. |
| 2011/0034890 A1 | 2/2011 | Stroebech et al. |
| 2011/0071482 A1 | 3/2011 | Selevan |
| 2011/0077497 A1 | 3/2011 | Oster et al. |
| 2011/0130642 A1 | 6/2011 | Jaeb et al. |
| 2011/0144470 A1 | 6/2011 | Mazar et al. |
| 2011/0191044 A1 | 8/2011 | Stafford |
| 2011/0245682 A1 | 10/2011 | Robinson et al. |
| 2011/0246983 A1 | 10/2011 | Brunet et al. |
| 2011/0257496 A1 | 10/2011 | Terashima et al. |
| 2012/0013130 A1 | 1/2012 | Jung |
| 2012/0089037 A1 | 4/2012 | Bishay et al. |
| 2012/0143154 A1 | 6/2012 | Edvardsen et al. |
| 2012/0143155 A1 | 6/2012 | Edvardsen et al. |
| 2012/0258302 A1 | 10/2012 | Hunt et al. |
| 2012/0283678 A1 | 11/2012 | Nguyen-Demary et al. |
| 2012/0304767 A1 | 12/2012 | Howard et al. |
| 2012/0323086 A1* | 12/2012 | Hansen ............... A61B 5/7475 600/300 |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0078912 A1 | 3/2013 | San Vicente et al. |
| 2013/0086217 A1 | 4/2013 | Price et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2013/0332085 A1* | 12/2013 | Yang ............... A61B 5/746 702/22 |
| 2014/0051946 A1 | 2/2014 | Arne et al. |
| 2014/0128815 A1 | 5/2014 | Cabiri et al. |
| 2014/0200426 A1 | 7/2014 | Taub et al. |
| 2014/0200538 A1 | 7/2014 | Euliano et al. |
| 2014/0236111 A1 | 8/2014 | Casado et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0057634 A1 | 2/2015 | Mastrototaro et al. |
| 2015/0150457 A1 | 6/2015 | Wu et al. |
| 2015/0151051 A1 | 6/2015 | Tsoukalis |
| 2015/0230706 A1 | 8/2015 | Nakagawa et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0272495 A1 | 10/2015 | Greener |
| 2015/0328389 A1 | 11/2015 | Heppe |
| 2015/0342777 A1 | 12/2015 | Seres et al. |
| 2015/0374896 A1 | 12/2015 | Du et al. |
| 2016/0008182 A1 | 1/2016 | Prokopuk et al. |
| 2016/0058604 A1 | 3/2016 | Wiltshire et al. |
| 2016/0084869 A1 | 3/2016 | Yuen et al. |
| 2016/0103966 A1 | 4/2016 | Mirza |
| 2016/0117062 A1 | 4/2016 | Hussam et al. |
| 2016/0158056 A1 | 6/2016 | Davis et al. |
| 2016/0158517 A1 | 6/2016 | Nebbia |
| 2016/0158969 A1 | 6/2016 | McLane et al. |
| 2016/0166438 A1 | 6/2016 | Rovaniemi |
| 2016/0178387 A1 | 6/2016 | Yamasaki et al. |
| 2016/0198996 A1* | 7/2016 | Dullen ............... A61B 5/4824 600/595 |
| 2016/0218555 A1 | 7/2016 | Slaby et al. |
| 2016/0235581 A1 | 8/2016 | Keleny et al. |
| 2016/0235582 A1 | 8/2016 | Moavenian |
| 2016/0242654 A1 | 8/2016 | Quinlan et al. |
| 2016/0267769 A1 | 9/2016 | Rokhsaz et al. |
| 2016/0278990 A1 | 9/2016 | Chen |
| 2016/0305776 A1 | 10/2016 | Mrtensson et al. |

(56) References Cited

U.S. PATENT DOCUMENTS

| | | |
|---|---|---|
| 2016/0310077 A1 | 10/2016 | Hunter et al. |
| 2016/0310140 A1 | 10/2016 | Belson et al. |
| 2016/0310329 A1 | 10/2016 | Patel et al. |
| 2016/0331232 A1 | 11/2016 | Love et al. |
| 2016/0331235 A1 | 11/2016 | Nyberg et al. |
| 2016/0361015 A1 | 12/2016 | Wang et al. |
| 2016/0363555 A1* | 12/2016 | Kang ................... G01N 27/407 |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0080236 A1* | 3/2017 | Karl ...................... A61N 1/3625 |
| 2017/0090236 A1 | 3/2017 | Yeh et al. |
| 2017/0098044 A1 | 4/2017 | Lai et al. |
| 2017/0113001 A1 | 4/2017 | Trock |
| 2017/0140103 A1 | 5/2017 | Angelides |
| 2017/0156920 A1 | 6/2017 | Hunt et al. |
| 2017/0181628 A1 | 6/2017 | Burnette et al. |
| 2017/0340474 A1 | 11/2017 | Thirstrup et al. |
| 2017/0340498 A1 | 11/2017 | Tessmer et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0049667 A1 | 2/2018 | Heppe |
| 2018/0055359 A1 | 3/2018 | Shamim et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0298240 A1 | 10/2018 | Chatterjee et al. |
| 2018/0318475 A1 | 11/2018 | Thomson et al. |
| 2019/0008439 A1 | 1/2019 | Sageder et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1* | 6/2019 | Hansen ................... G08C 17/02 |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0252079 A1 | 8/2019 | Constantin et al. |
| 2019/0374163 A1 | 12/2019 | Faarbaek et al. |
| 2020/0000624 A1* | 1/2020 | Gibbons ................. A61B 5/444 |
| 2020/0078206 A1 | 3/2020 | Chiladakis |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencía |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1* | 10/2020 | Hansen ................. A61F 5/4404 |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1* | 12/2020 | Hansen ................. A61B 5/6832 |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1* | 1/2021 | Hansen ................... G01K 13/00 |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0145354 A1 | 5/2021 | Hunt et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1* | 12/2021 | Hansen ................. A61B 5/7435 |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1 | 1/2022 | Thirstrup et al. |
| 2022/0031227 A1 | 2/2022 | Cho et al. |
| 2022/0031495 A1 | 2/2022 | Seres et al. |
| 2022/0079802 A1* | 3/2022 | Hansen ................. A61F 5/4404 |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0304844 A1 | 9/2022 | Carlsson et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0141297 A1 | 5/2023 | Herold et al. |
| 2023/0141719 A1 | 5/2023 | Emborg et al. |
| 2023/0142141 A1 | 5/2023 | Emborg et al. |
| 2023/0145670 A1 | 5/2023 | Seres et al. |
| 2023/0146436 A1 | 5/2023 | Hansen et al. |
| 2023/0147665 A1 | 5/2023 | Hasbeck et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0255811 A1 | 8/2023 | Carlsson et al. |
| 2023/0284932 A1* | 9/2023 | Hansen ................... G06T 7/0012 |
| 2023/0293333 A1* | 9/2023 | Hansen .................... A61F 5/445 |
| | | 604/318 |
| 2023/0293335 A1* | 9/2023 | Hansen .................... A61F 5/443 |
| | | 604/344 |
| 2023/0301818 A1* | 9/2023 | Hansen ............... A61L 24/0031 |
| 2023/0310201 A1* | 10/2023 | Hansen .................... A61F 5/445 |
| 2023/0329893 A1 | 10/2023 | Olsen et al. |
| 2023/0338005 A1 | 10/2023 | Barthe et al. |

(56) References Cited

U.S. PATENT DOCUMENTS

| | | | |
|---|---|---|---|
| 2023/0372141 A1* | 11/2023 | Larsen | A61F 5/443 |
| 2023/0414397 A1* | 12/2023 | Hansen | A61F 5/4404 |
| 2024/0009020 A1 | 1/2024 | Hansen et al. | |
| 2024/0041635 A1* | 2/2024 | Hansen | A61B 5/4851 |
| 2024/0164933 A1* | 5/2024 | Hansen | A61F 5/445 |
| 2024/0180740 A1 | 6/2024 | Hansen et al. | |
| 2024/0225539 A1 | 7/2024 | Svanegaard et al. | |
| 2024/0261130 A1 | 8/2024 | Hansen et al. | |

FOREIGN PATENT DOCUMENTS

| | | | |
|---|---|---|---|
| CA | 3009449 C | 9/2019 | |
| CA | 3002372 C | 3/2021 | |
| CA | 2947016 C | 2/2023 | |
| CN | 103269668 A | 8/2013 | |
| CN | 203786580 U | 8/2014 | |
| CN | 104902399 A | 9/2015 | |
| CN | 104980878 A | 10/2015 | |
| CN | 105588856 A | 5/2016 | |
| CN | 106062546 A | 10/2016 | |
| CN | 206271160 U | 6/2017 | |
| CN | 206450708 U | 8/2017 | |
| CN | 105615896 B | 5/2019 | |
| CN | 105359167 B | 6/2019 | |
| DE | 3437950 A1 | 4/1985 | |
| DE | 3836590 A1 | 5/1990 | |
| DE | 19953062 A1 | 5/2000 | |
| DE | 19900611 C1 | 7/2000 | |
| DE | 102011014321 A1 | 9/2012 | |
| DE | 102011076219 A1 | 11/2012 | |
| EP | 0168967 A1 | 1/1986 | |
| EP | 0373782 A1 | 6/1990 | |
| EP | 0416397 A1 | 3/1991 | |
| EP | 0850076 B1 | 4/2005 | |
| EP | 1188157 B1 | 12/2005 | |
| EP | 2108345 A1 | 10/2009 | |
| EP | 2489561 A2 | 8/2012 | |
| EP | 2654646 A2 | 10/2013 | |
| EP | 2453851 B1 | 10/2014 | |
| EP | 3064179 A1 | 9/2016 | |
| EP | 3213727 A1 | 9/2017 | |
| GB | 2219679 A | 12/1989 | |
| GB | 2225951 A | 6/1990 | |
| GB | 2343628 A | 5/2000 | |
| GB | 2465742 A | 6/2010 | |
| GB | 2542093 A | 3/2017 | |
| JP | 04-074882 A | 3/1992 | |
| JP | 06-152077 A | 5/1994 | |
| JP | 09-010184 A | 1/1997 | |
| JP | 11-128352 A | 5/1999 | |
| JP | 2000-093448 A | 4/2000 | |
| JP | 2001-087299 A | 4/2001 | |
| JP | 2002-055074 A | 2/2002 | |
| JP | 2002-224093 A | 8/2002 | |
| JP | 2005-323981 A | 11/2005 | |
| JP | 2007-319561 A | 12/2007 | |
| JP | 2014-033745 A | 2/2014 | |
| JP | 2014-054368 A | 3/2014 | |
| JP | 2014-507182 A | 3/2014 | |
| JP | 2014151096 A | 8/2014 | |
| KR | 10-2012-0003987 A | 1/2012 | |
| NL | 1003904 C2 | 3/1998 | |
| RU | 2527155 C2 | 8/2014 | |
| TW | 201201783 A | 1/2012 | |
| WO | 94/15562 A1 | 7/1994 | |
| WO | 97/10012 A1 | 3/1997 | |
| WO | 99/33037 A1 | 7/1999 | |
| WO | 99/36017 A1 | 7/1999 | |
| WO | 00/79497 A1 | 12/2000 | |
| WO | 01/13830 A1 | 3/2001 | |
| WO | 01/50996 A1 | 7/2001 | |
| WO | 02/52302 A2 | 7/2002 | |
| WO | 02/99765 A1 | 12/2002 | |
| WO | 2004084778 A2 | 10/2004 | |
| WO | 2005/038693 A1 | 4/2005 | |
| WO | 2005/082271 A2 | 9/2005 | |
| WO | 2006/008866 A1 | 1/2006 | |
| WO | 2006/094513 A2 | 9/2006 | |
| WO | 2007/000168 A1 | 1/2007 | |
| WO | 2007/059774 A2 | 5/2007 | |
| WO | 2007/070266 A1 | 6/2007 | |
| WO | WO-2007098762 A1 * | 9/2007 | A61B 5/746 |
| WO | 2007/133555 A2 | 11/2007 | |
| WO | 2007128038 A1 | 11/2007 | |
| WO | 2008/057884 A2 | 5/2008 | |
| WO | 2009/006900 A1 | 1/2009 | |
| WO | 2009/052496 A1 | 4/2009 | |
| WO | 2009/107011 A1 | 9/2009 | |
| WO | 2009/112912 A2 | 9/2009 | |
| WO | 2011/003421 A1 | 1/2011 | |
| WO | 2011/004165 A1 | 1/2011 | |
| WO | 2011003420 A1 | 1/2011 | |
| WO | 2011/061540 A1 | 5/2011 | |
| WO | 2011/105701 A2 | 9/2011 | |
| WO | 2011/123018 A1 | 10/2011 | |
| WO | 2011/139499 A1 | 11/2011 | |
| WO | 2011/161254 A2 | 12/2011 | |
| WO | 2012/068386 A1 | 5/2012 | |
| WO | 2012/076022 A2 | 6/2012 | |
| WO | 2012/084987 A2 | 6/2012 | |
| WO | 2013/013197 A1 | 1/2013 | |
| WO | 2013095231 A1 | 6/2013 | |
| WO | 2013164517 A1 | 11/2013 | |
| WO | 2014/004207 A1 | 1/2014 | |
| WO | 2014/086369 A1 | 6/2014 | |
| WO | 2014116816 A1 | 7/2014 | |
| WO | 2015/007284 A1 | 1/2015 | |
| WO | 2015/014774 A1 | 2/2015 | |
| WO | 2015/084462 A1 | 6/2015 | |
| WO | 2015/094064 A1 | 6/2015 | |
| WO | 2015/187366 A1 | 12/2015 | |
| WO | 2016/132738 A1 | 8/2016 | |
| WO | 2016124202 A1 | 8/2016 | |
| WO | 2016/166731 A1 | 10/2016 | |
| WO | 2016162038 A1 | 10/2016 | |
| WO | 2016/192738 A1 | 12/2016 | |
| WO | 2017/023794 A1 | 2/2017 | |
| WO | 2017/062042 A1 | 4/2017 | |
| WO | 2017/067558 A1 | 4/2017 | |
| WO | 2017/067560 A1 | 4/2017 | |
| WO | 2017/074505 A1 | 5/2017 | |
| WO | 2017/088153 A1 | 6/2017 | |
| WO | 2017108109 A1 | 6/2017 | |
| WO | 2017/136696 A1 | 8/2017 | |
| WO | 2017/190752 A1 | 11/2017 | |
| WO | 2018/028756 A1 | 2/2018 | |
| WO | 2019/094635 A1 | 5/2019 | |
| WO | 2019/120432 A1 | 6/2019 | |
| WO | 2019/161859 A1 | 8/2019 | |
| WO | 2019/161860 A1 | 8/2019 | |
| WO | 2019/161863 A1 | 8/2019 | |
| WO | 2019/174693 A1 | 9/2019 | |
| WO | 2019/174695 A1 | 9/2019 | |
| WO | 2019/213623 A1 | 11/2019 | |
| WO | 2020/035121 A1 | 2/2020 | |

* cited by examiner

APPLICATION OF A STOMAL SENSOR PATCH

The present disclosure relates to application of a sensor patch to an adhesive base plate for an ostomy appliance. In particular the present disclosure relates to ways of sensing application and/or failure of application of such.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY

It is an object of the present disclosure to provide a sensor patch for facilitating reliable and/or improved detection of risk of failure of an ostomy appliance and/or improved detection of risk of leakage. The sensor patch may be provided to facilitate detection of risk of failure and/or risk of leakage with respect to an adhesive base plate of the ostomy appliance.

A base plate may comprise: at least a first layer of an adhesive material, e.g. a first adhesive layer, adapted for attachment of the base plate to the skin surface of a user; a backing layer comprising a film material and having a distal surface and a proximal surface; and a centre portion surrounding a stoma-receiving opening extending through the base plate.

It is a further object of the present disclosure to provide ways of facilitating correct attachment of a sensor patch to an ostomy appliance, such as a base plate of the ostomy appliance, such as to enhance reliability of measurements performed by the use of a sensor patch. The measurements/monitoring may be performed by an ostomy system comprising the base plate, the sensor patch, and a monitor device couplable to the sensor patch. In particular, it is an object to provide a method for detecting whether a sensor patch, for attachment to a base plate, has been sufficiently attached the base plate. According to embodiments of the invention, the sensor patch is to be attached to the adhesive surface of a base plate, such as a generic base plate in the field of ostomy appliances, by the user. However, in order to provide a reliable monitoring of adhesive performance and/or presence of liquid in the interface between the skin surface and the adhesive of the sensor patch and/or base plate, it is important for the ostomy system to know, whether the sensor patch has been attached to the base plate with such an accuracy that the sensor readings are reliable. In other words, it is an object of the invention to evaluate the attachment of a sensor patch to a base plate, in particular prior to assessing the adhesive performance and/or presence of liquid in the interface between the skin surface and the adhesive of the sensor patch and/or base plate.

Accordingly, a sensor patch for attachment to a base plate for an ostomy appliance is disclosed. The sensor patch is adapted for attachment to a proximal side of the base plate, such as a first layer of the base plate, such as a first adhesive layer of the base plate. The sensor patch comprises a sensor assembly comprising a plurality of electrodes including a first electrode and a second electrode for forming a first sensor.

Also disclosed is a method for evaluating attachment of a sensor patch, such as the disclosed sensor patch, to a base plate for an ostomy appliance. The method comprising: measuring one or more characteristic quantities; and determining whether the one or more characteristic quantities satisfies one or more attachment criteria.

Also disclosed is a monitor device for evaluating attachment of a sensor patch, such as the disclosed sensor patch, to a base plate for an ostomy appliance. The monitor device may be configured to perform the disclosed method and/or at least part of the disclosed method. The monitor device may be configured to: measure one or more characteristic quantities; and determine whether the one or more characteristic quantities satisfies one or more attachment criteria.

BRIEF DESCRIPTION OF THE FIGURES

Embodiments of the disclosure will be described in more detail in the following with regard to the accompanying figures. The figures show one way of implementing the present invention and are not to be construed as being limiting to other possible embodiments falling within the scope of the attached claim set.

DETAILED DESCRIPTION

Figure 1:
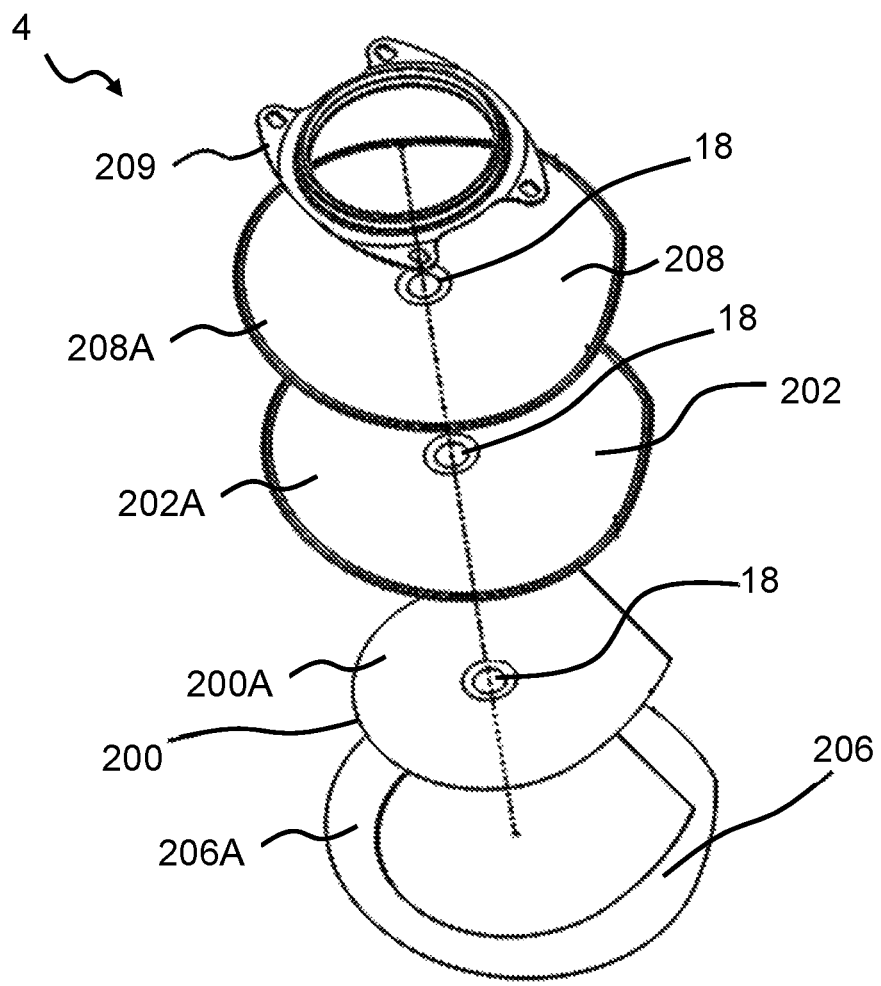
FIG. 1 schematically illustrates an exploded view of an exemplary base plate.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him—or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

FIG. 1 schematically illustrates an exploded view of an exemplary base plate 4 of an ostomy appliance. The base plate 4 comprises a first adhesive layer 200, i.e. a first layer of an adhesive material. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, i.e. a second layer of an adhesive material, also denoted rim adhesive layer. The second adhesive layer 202 may be of a different adhesive material than the first adhesive layer 200. The base plate 4 may comprise a release liner 206, which may be peeled off by the user prior to applying the base plate 4 to the skin. The base plate 4 comprises a backing layer 208. The backing layer 208 is a protective layer protecting the adhesive layers, such as the first adhesive layer 200 and/or the second adhesive layer 202 from external strains and stress during use. Furthermore, the backing layer 208 also covers the adhesive layers, such as the first adhesive layer 200 and/or the second adhesive layer 202, such that the adhesive layers 200,202 does not adhere to clothes worn on top of the base plate 4.

The base plate 4, as illustrated, is a two-part ostomy appliance, thus comprising a coupling ring 209 for coupling an ostomy pouch to the base plate 4.

The first adhesive layer 200 may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids.

The second adhesive layer 202 may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids.

Different ratio of contents may change properties of the first adhesive layer 200 and/or the second adhesive layer 202. The second adhesive layer 202 and the first adhesive layer 200 may have different properties. The second adhesive layer 202 (second composition) and the first adhesive layer 200 (first composition) may have different ratios of polyisobutenes, styrene-isoprene-styrene, and/or hydrocolloids. For example, the second adhesive layer 202 may provide a stronger attachment to the skin compared to attachment to the skin provided by the first adhesive layer 200. Alternatively or additionally, the second adhesive layer 202 may be thinner than the first adhesive layer 200. Alternatively or additionally, the second adhesive layer 202 may be less water and/or sweat absorbing than the first adhesive layer 200. Alternatively or additionally, the second adhesive layer 202 may be less mouldable than the first adhesive layer 200. The second adhesive layer 202 may provide a second barrier against leakage.

The first adhesive layer 200 comprises a distal surface 200A and a proximal surface (not shown). The proximal surface of the first adhesive layer 200 is configured to adhere to the user's skin, and the distal surface 200A of the first adhesive layer 200 is configured to face away from the skin of the user. The second adhesive layer 202 comprises a distal surface 202A and a proximal surface (not shown). The proximal surface of the second adhesive layer 202 is configured to adhere to the user's skin, at least at a rim portion of the second adhesive layer 202, and the distal surface 202A of the second adhesive layer 202 is configured to face away from the skin of the user. The second adhesive layer 202 is covering a larger area than the first adhesive layer 200, such that the proximal surface of the second adhesive layer 202 forms an adhesive rim surrounding the first adhesive layer 200.

The release liner 206 comprises a distal surface 206A and a proximal surface (not shown). The distal surface 206A of the release liner 206 is covering the proximal surface of the first adhesive layer 200 and covering the proximal surface of the second adhesive layer 202 not covered by the first adhesive layer 200.

The backing layer 208 comprises a distal surface 208A and a proximal surface (not shown). The distal surface 208A of the backing layer 208 is configured to face away from the skin of the user. The proximal surface of the backing layer 208 is covering the second adhesive layer 202.

The base plate 4 comprises a stomal opening 18. Each layer of the base plate 4 may comprise stomal openings for collectively forming the stomal opening 18 of the base plate. The stomal opening 18 is provided in a centre portion of the base plate 4 surrounding the stomal opening 18.

The stomal opening 18 may be configured to receive a stoma of the user and/or the stomal opening 18 may be configured to allow output from the stoma to pass through the stomal opening an into an ostomy pouch attached to the base plate 4. For example, the stomal opening may be configured to allow passage of output from the proximal side of the base plate 4 to a distal side of the base plate 4. The size and/or shape of the stomal opening may typically be adjusted by the user or nurse before application of the base plate 4 to accommodate the user's stoma.

Figure 2:
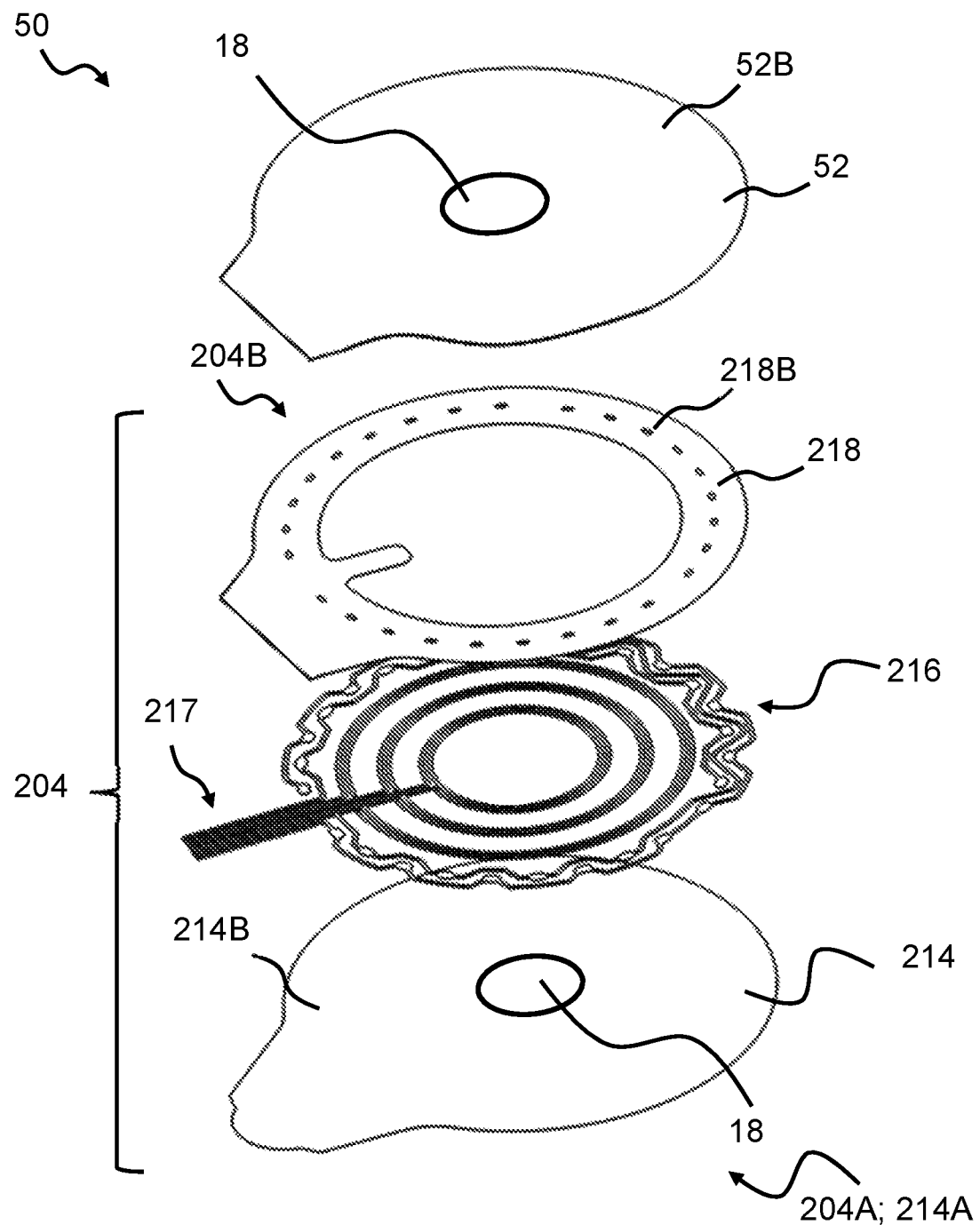
FIG. 2 schematically illustrates an exploded view of an exemplary sensor patch.

FIG. 2 schematically illustrates an exploded view of an exemplary sensor patch 50 being adapted for attachment to a base plate of an ostomy appliance, such as the base plate as illustrated in FIG. 1. The sensor patch 50 is configured to be positioned between the skin of the user and the proximal side of the base plate 4. For example, the sensor patch may be adapted for attachment to the first adhesive layer 200 of the base plate 4.

The sensor patch 50 is configured to facilitate detection of moisture propagation in the adhesive material provided for attaching the base plate to the skin surface of a user as well as detection of increased risk of leakage. The sensor patch 50 comprises a sensor assembly 204 comprising a plurality of electrodes 216. The plurality of electrode 216 includes a first electrode and a second electrode for forming a first sensor. The electrodes 216 including a ground electrode, a first electrode, a second electrode, a third electrode, a fourth electrode, and a fifth electrode. Each electrode has respective connection parts 217 for connecting the electrodes 216 to respective terminal elements of a monitor device. The sensor assembly 204 may form a sensor assembly layer.

The sensor assembly 204 has a distal side 204A and a proximal side 204B. The sensor assembly 204 comprises a support layer 214 with a proximal surface 214B. The electrodes 216 are provided, such as formed, on the proximal surface 214B of the support layer 214, e.g. the electrodes 216 may be positioned on the proximal surface 214B of the support layer 214.

The electrode assembly 204 may comprise a masking element 218, as illustrated, with a proximal surface 218B and configured to electrically insulate at least parts of electrodes 216 from adjacent layers, such as an adhesive sensor layer 52. The masking element 218 covers or overlap with parts of the electrodes 216 when seen in the axial direction.

The sensor patch 50 is configured to be positioned on the base plate, such that the distal side of the sensor patch 50, such as the distal surface 204A of the sensor assembly 204 is coupled to the adhesive proximal surface of the base plate. The sensor patch 50 further comprises an optional adhesive sensor layer 52, with a proximal side 52B and a distal side (not visible). The adhesive sensor layer 52 is arranged on a proximal side of the sensor assembly 204. The proximal side 52B of the adhesive sensor layer 52 is configured to adhere to the user's skin. Thus, after being applied to the base plate, the combined base plate and sensor patch 50 may form an adhesive proximal surface configured to be applied to the skin surface of the user.

The adhesive sensor layer 52 may be made of a third composition. The third composition may comprise one or more polyisobutenes and/or styrene-isoprene-styrene. The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids. The third composition may be the same as the first composition. The adhesive sensor layer 50 may be made of the first composition.

The sensor patch 50 comprises a stomal opening 18. Each layer of the sensor patch 50 may comprise stomal openings for collectively forming the stomal opening 18 of the sensor patch 50. The stomal opening 18 of the sensor patch is configured to be aligned with the stomal opening of the base plate, such as to collectively forming the stomal opening of the combined base plate and sensor patch 50. The size and/or shape of the stomal opening of the sensor patch 50 may be adjusted by the user or nurse before application of the sensor patch 50 to accommodate the user's stoma. The size and/or shape of the stomal opening of the sensor patch 50 may be adjusted together with adjustment of the stomal opening of the base plate, e.g. after the sensor patch 50 is attached to the base plate.

The sensor patch 50 may comprise a monitor interface (not shown). The monitor interface may be configured for electrically and/or mechanically connecting the sensor patch 50, such as the electrodes 216 of the sensor patch 50, to the monitor device. The monitor interface may be configured for wirelessly connecting the sensor patch 50, such as the electrodes 216 of the sensor patch to the monitor device. The monitor interface of the sensor patch 50 may be configured to electrically and/or mechanically couple the sensor patch 50 and the monitor device.

Figure 3:
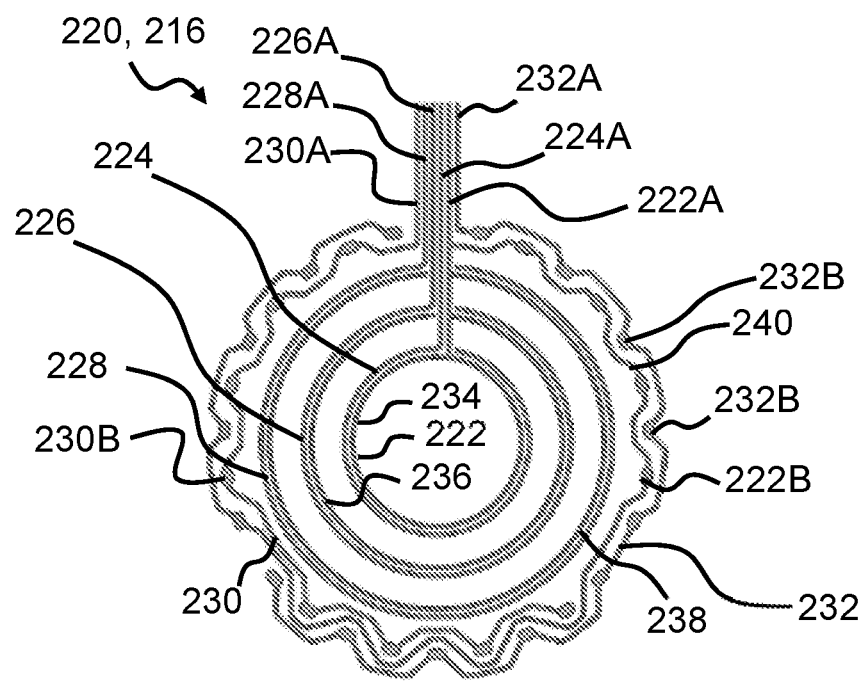
FIG. 3 schematically illustrates an exemplary electrode configuration.

FIG. 3 schematically illustrates an exemplary electrode configuration 220 of electrodes 216 of an exemplary sensor assembly, such as the sensor assembly 204 as described with respect to FIG. 2. The sensor assembly 204 may comprise one or more electrodes, such as a plurality of electrodes, such as two, three, four, five, six, seven or more electrodes. In the illustrated example, the electrode configuration 220 comprises a ground electrode 222, a first electrode 224, a second electrode 226, a third electrode 228, a fourth electrode 230, and a fifth electrode 232.

The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

The electrodes 216 are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the plurality of electrodes 216 may form a sensor. A first electrode and a second electrode may form a first sensor. For example, the first electrode 224 and the ground electrode 222 (e.g. first electrode part of the ground electrode) may form a first sensor or first electrode pair. The second electrode 226 and the ground electrode 222 (e.g. second electrode part of the ground electrode) may form a second sensor or second electrode pair. The third electrode 228 and the ground electrode 222 (e.g. third electrode part of the ground electrode) may form a third sensor or third electrode pair. The fourth electrode 230 and the ground electrode 222 (e.g. fourth electrode part of the ground electrode) may form a fourth sensor or fourth electrode pair. The fifth electrode 232 and the ground electrode 222 (e.g. fifth electrode part of the ground electrode) may form a fifth sensor or fifth electrode pair.

The electrodes may form loops and/or open loops. The first electrode 224 may form an open loop. The second electrode 226 may form an open loop and/or the third 228 electrode may form an open loop. The fourth electrode 230 may form an open loop. The fifth electrode 232 may form an open loop. Open loop electrode(s) enables electrode arrangement in few or a single electrode layer.

Figure 4A:
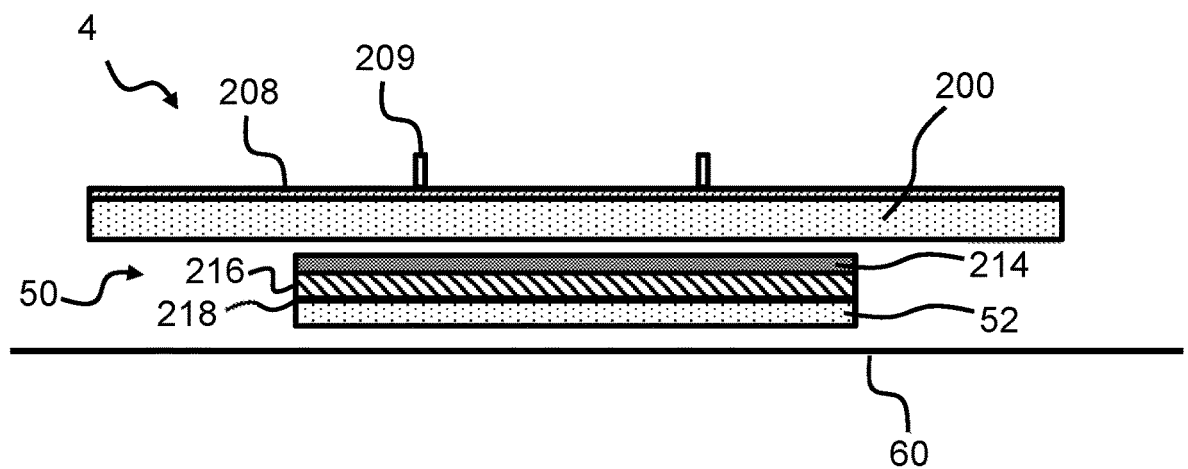
FIGS. 4a and 4b schematically illustrate a base plate, a sensor patch and a skin surface of a user, FIG. 5 schematically illustrates an exploded view of an exemplary sensor patch, FIG. 6 schematically illustrates an exploded view of an exemplary sensor patch.
Figure 4B:
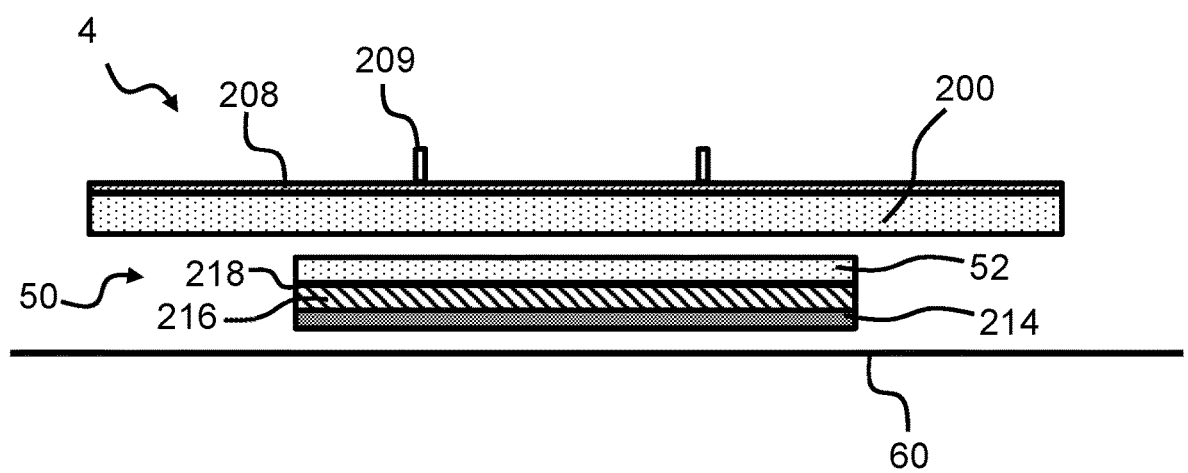

FIG. 4*a* and FIG. 4*b* schematically illustrates a base plate 4, a sensor patch 50 and a skin surface 60 of a user. The base plate 4 comprises a first adhesive layer 200, a backing layer 208 and a coupling ring 209, as further described in relation to FIG. 1. The sensor patch 50 comprises a plurality of electrodes 216, a support layer 214, a masking element 218, and an adhesive sensor layer 52, as further described in relation to FIG. 2.

FIG. 4*a* schematically illustrates the sensor patch 50 being orientated between the base plate 4 and the skin surface 60 of the user, such that the adhesive sensor layer 52 is facing towards the skin surface 60 of the user. Thus, the adhesive sensor layer 52 is adhering to the skin surface 60 of the user throughout the area of the first adhesive layer 200 being covered by the sensor patch 50.

The orientation of the sensor patch 50 relative to the base plate 4, as illustrated in FIG. 4*a*, is the preferred orientation of the sensor patch, which facilitates correct measuring by the electrodes 216.

FIG. 4*b* schematically illustrates the sensor patch 50 being orientated between the base plate 4 and the skin surface 60 of the user, such that the adhesive sensor layer 52 is facing away from the skin surface 60 of the user and towards the first adhesive layer 200 of the base plate 4. Thus, the adhesive sensor layer 52 will be adhering to the first adhesive layer 200, and no adhesive is provided through the area being covered by the sensor patch 50.

The orientation of the sensor patch 50 relative to the base plate 4, as illustrated in FIG. 4*b*, is a non-preferred orientation of the sensor patch, as it may compromise measuring by the electrodes 216, since the support layer 214, which may be electrically insulative, is positioned between the electrodes 216 and the skin surface 60 of the user. Furthermore, the part of the adhesive layers being subjective to measurement by the electrodes 216 is shielded from the skin surface 60 of the user by the support layer 214. Hence, measurements may be unreliable to detect moisture content in the adhesives as well as leakage.

By use of electrical measurements of the electrodes 216, the orientation of the sensor patch 50 relative to the base plate 4, may be determined. For example, measurements of resistance and/or capacitance between two or more of the electrodes 216 may be indicative of the orientation of the sensor patch 50 relative to the base plate 4. Thus, the user may be notified if he/she has attached the sensor patch 50 incorrectly, as illustrated in FIG. 4*b*, and/or the user may be notified if he/she has attached the sensor patch 50 correctly, as illustrated in FIG. 4*a*. Such measurement may be performed after the sensor patch 50 is attached to the base plate 4 and/or after the sensor patch 50 and base plate 4 has been attached to the skin of the user.

Figure 5:
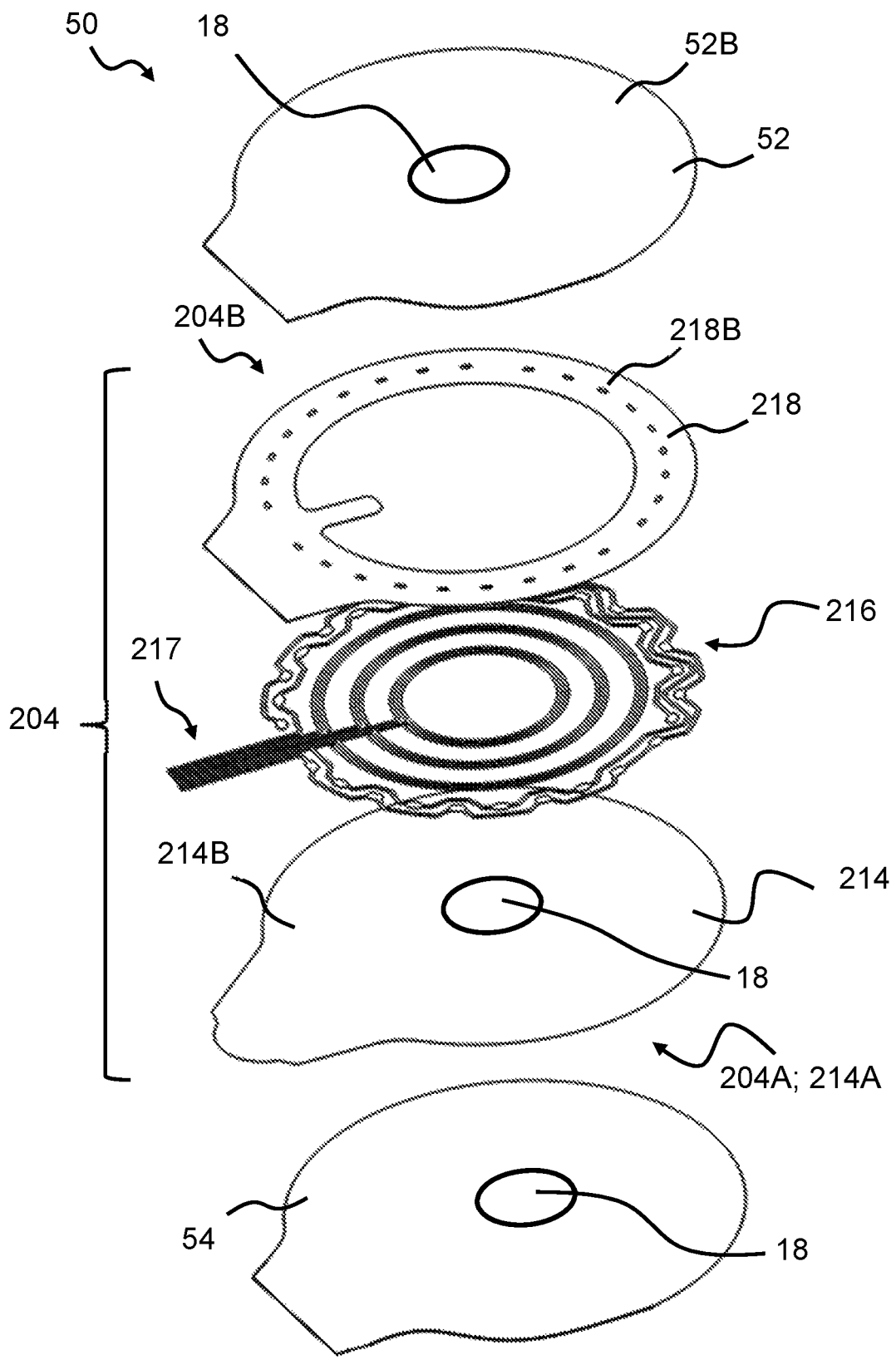

FIG. 5 schematically illustrates an exploded view of an exemplary sensor patch 50, such as the sensor patch 50 as illustrated in FIG. 2. However, the sensor patch 50 as illustrated in FIG. 5 comprises an additional optional layer, namely a shielding layer 54. The shielding layer 54 is of an electrically conductive material, and the shielding layer 54 is arranged on a distal side of the sensor assembly 204. Thus, when the sensor patch 50 is arranged as intended relative to the base plate, the shielding layer 54 is positioned between the sensor assembly 204 and the first adhesive layer of the base plate. This may further enhance the determination of orientation of the sensor patch 50 relative to the base plate.

Figure 6:
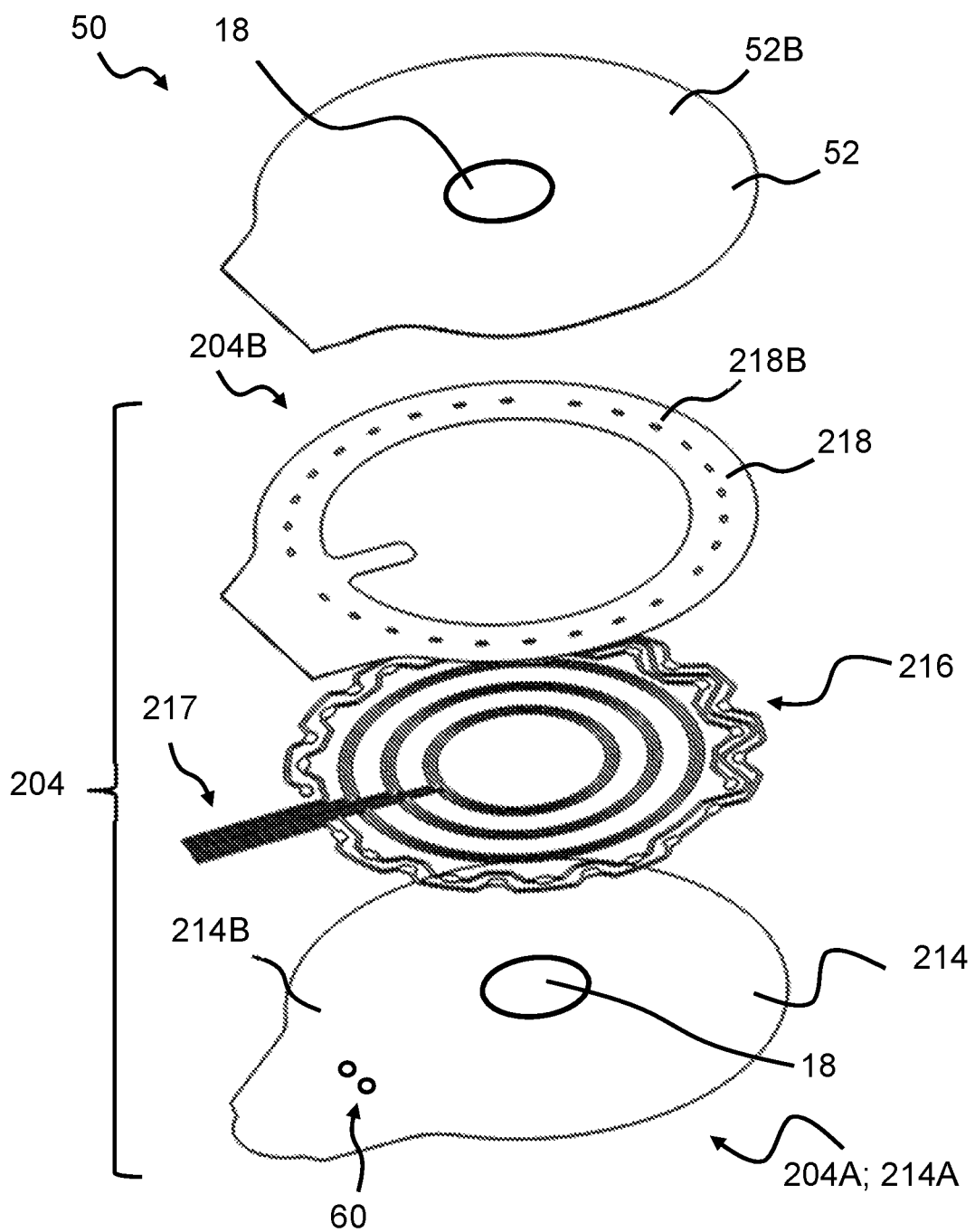

FIG. 6 schematically illustrates an exploded view of an exemplary sensor patch 50, such as the sensor patch 50 as illustrated in FIG. 2 and FIG. 5. However, the support layer 214 of the sensor patch 50 as illustrated in FIG. 6 comprises detection openings 60, such as a first detection opening and a second detection opening. The detection openings 60 may provide a contact surface between the adhesive surface of the base plate and two or more of the plurality of electrodes 216 of the sensor patch 50. Thereby, the conductivity between the two or more of the plurality of electrodes 216 may be altered by the conductivity of the adhesive of the base plate, thereby providing another or additional option for determining which side of the sensor patch is facing the adhesive of the base plate. This may further enhance the determination of orientation of the sensor patch 50 relative to the base plate.

The exemplary support layer 214 as illustrated in FIG. 6 may be provided in combination with the shielding layer 54 of FIG. 5, whereas the shielding layer 54 may also be provided with detection openings to provide for the adhesive of the base plate to contact two or more of the plurality of electrodes 216.

The plurality of electrodes 216 may comprise designated attachment detection electrodes, such as a first attachment detection electrode and/or a second attachment detection electrode. The first attachment detection electrode and/or the second attachment detection electrode may be exposed by the detection openings 60. Alternatively, electrodes, such as the first electrode and/or the second electrode, forming a sensor, such as the first sensor, may be exposed by the detection openings 60.

Figure 7:
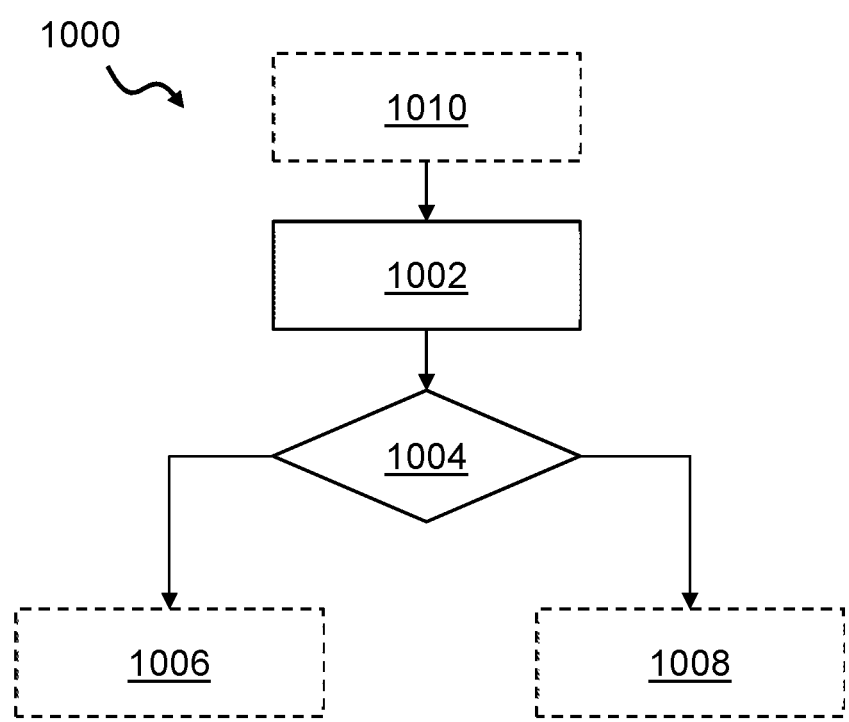
FIG. 7 is a schematic block diagram of an exemplary method.

FIG. 7 is a schematic block diagram of an exemplary method 1000 for evaluating attachment of a sensor patch to a base plate, such as a sensor patch and a base plate as described with respect to the previous figures.

The method comprises measuring 1002 one or more characteristic quantities and determining 1004 whether the one or more characteristic quantities satisfies one or more attachment criteria. In embodiments, the method comprises the additional step of attaching the sensor patch to the adhesive surface or to the backing layer of a baseplate. In embodiments, the sensor patch is attached to the adhesive surface or to the backing layer of a baseplate prior to measuring the one or more characteristic quantities. Measuring 1002 the one or more characteristic quantities and/or determining 1004 whether the one or more characteristic quantities satisfies the one or more attachment criteria may be performed prior to attachment of the base plate to the skin of the user. Alternatively, measuring 1002 the one or more characteristic quantities and/or determining 1004 whether the one or more characteristic quantities satisfies the one or more attachment criteria may be performed after attachment of the base plate to the skin of the user. In embodiments, measuring 1002 the one or more characteristic quantities and/or determining 1004 whether the one or more characteristic quantities satisfies the one or more attachment criteria is performed after attachment of the base plate to the skin of the user, but before measuring characteristics pertaining to the adhesive performance of the sensor patch and/or assessing whether liquid is presence in the interface between the skin surface of the user and the sensor patch and/or base plate. In other words, the evaluation of attachment may be performed after attaching the base plate with the sensor patch to the skin surface of the user, but before evaluating adhesive performance and/or presence of liquid in the interface.

Thereby, in the case of insufficient attachment of the sensor patch to the base plate, the risk of leakage is reduced, as no determinations/conclusions based on the sensors of the sensor patch are made before the attachment as such has been evaluated according to the disclosed method. Rather, if insufficient attachment has been determined, the user may be requested to change/remove his/her base plate and sensor patch. In other words, in embodiments, the sensors for monitoring the adhesive performance and/or detecting presence of liquid (output) are not active until the disclosed method for evaluating attachment of a sensor patch to a base plate has been carried out.

The measured 1002 one or more characteristic quantities may include a first characteristic quantity being indicative of electrical capacitance between the electrodes, such as between a first electrode and a second electrode. Measuring 1002 the one or more characteristic quantities may comprise measuring capacitance and/or resonance frequency between the electrodes, e.g. between two electrodes, e.g. between the first electrode and the second electrode. The first electrode and/or the second electrode may be designated attachment detection electrodes, such as the first attachment detection electrode and/or the second attachment detection electrode as described with respect to FIG. 6. Alternatively, the first electrode and/or the second electrode may be the first electrode and the second electrode forming a sensor, such as the first sensor.

Determining 1004 whether the one or more characteristic quantities satisfies the one or more attachment criteria may comprise comparing the first characteristic quantity and a first characteristic threshold value. For the one or more characteristic quantities to satisfy the one or more attachment criteria it may be required that the first characteristic quantity is above the first characteristic threshold value. Alternatively or additionally, for the one or more characteristic quantities to satisfy the one or more attachment criteria it may be required that the first characteristic quantity is below a first secondary characteristic threshold value. Alternatively or additionally, for the one or more characteristic quantities to satisfy the one or more attachment criteria it may be required that the first characteristic quantity is below the first characteristic threshold value.

The measured 1002 one or more characteristic quantities may include a second characteristic quantity being indicative of electrical resistance between the electrodes, such as between the first electrode and the second electrode. Measuring 1002 the one or more characteristic quantities may comprise measuring resistance between the electrodes, e.g. between two electrodes, e.g. between the first electrode and the second electrode. The first electrode and/or the second electrode may be designated attachment detection electrodes, such as the first attachment detection electrode and/or the second attachment detection electrode as described with respect to FIG. 6. Alternatively, the first electrode and/or the second electrode may be the first electrode and the second electrode forming a sensor, such as the first sensor.

Determining 1004 whether the one or more characteristic quantities satisfies the one or more attachment criteria may comprise comparing the second characteristic quantity and a second characteristic threshold value. For the one or more characteristic quantities to satisfy the one or more attachment criteria it may be required that the second characteristic quantity is above the second characteristic threshold value. Alternatively or additionally, for the one or more characteristic quantities to satisfy the one or more attachment criteria it may be required that the second characteristic quantity is below a second secondary characteristic threshold value. Alternatively or additionally, for the one or more characteristic quantities to satisfy the one or more attachment criteria it may be required that the second characteristic quantity is below the second characteristic threshold value.

Determining 1004 whether the one or more characteristic quantities satisfies the one or more attachment criteria may comprise comparing a third characteristic quantity and a third characteristic threshold value. The third characteristic quantity may be based on the first characteristic quantity and the second characteristic quantity. For example, the third characteristic quantity may be an algebraic expression comprising the first characteristic quantity and the second characteristic quantity.

Determining 1004 whether the one or more characteristic quantities satisfies the one or more attachment criteria may comprise comparing the third characteristic quantity and a third characteristic threshold value. For the one or more characteristic quantities to satisfy the one or more attachment criteria it may be required that the third characteristic quantity is above the third characteristic threshold value. Alternatively or additionally, for the one or more characteristic quantities to satisfy the one or more attachment criteria it may be required that the third characteristic quantity is below a third secondary characteristic threshold value. Alternatively or additionally, for the one or more characteristic quantities to satisfy the one or more attachment criteria it may be required that the third characteristic quantity is below the third characteristic threshold value.

The method 1000 optionally comprises in accordance with the one or more characteristic quantities not satisfying the one or more attachment criteria, issuing 1006 a failure signal indicative of the sensor patch not being sufficiently attached.

The method 1000 optionally comprises in accordance with the one or more characteristic quantities satisfying the one or more attachment criteria, issuing 1008 a success signal indicative of the sensor patch being sufficiently attached.

The sensor patch may comprise a monitor interface configured for connecting the sensor assembly to a monitor device. The method 1000 may comprise connecting 1010 the monitor device to the sensor assembly, e.g. prior to measuring 1002 the one or more characteristic quantities. Measuring 1002 the one or more characteristic quantities and/or determining 1004 whether the one or more characteristic quantities satisfies the one or more attachment criteria may be performed by the monitor device. Issuing 1006 the failure signal may be performed by the monitor device and/or by an auxiliary device coupled to the monitor device. Issuing 1008 the success signal may be performed by the monitor device and/or by an auxiliary device coupled to the monitor device. An auxiliary device may be wirelessly coupled to the monitor device. An auxiliary device may be a mobile phone, such as a smartphone, a smartwatch, a tablet, a computer, or the like, capable of issuing and/or displaying notifications.

Figure 8:
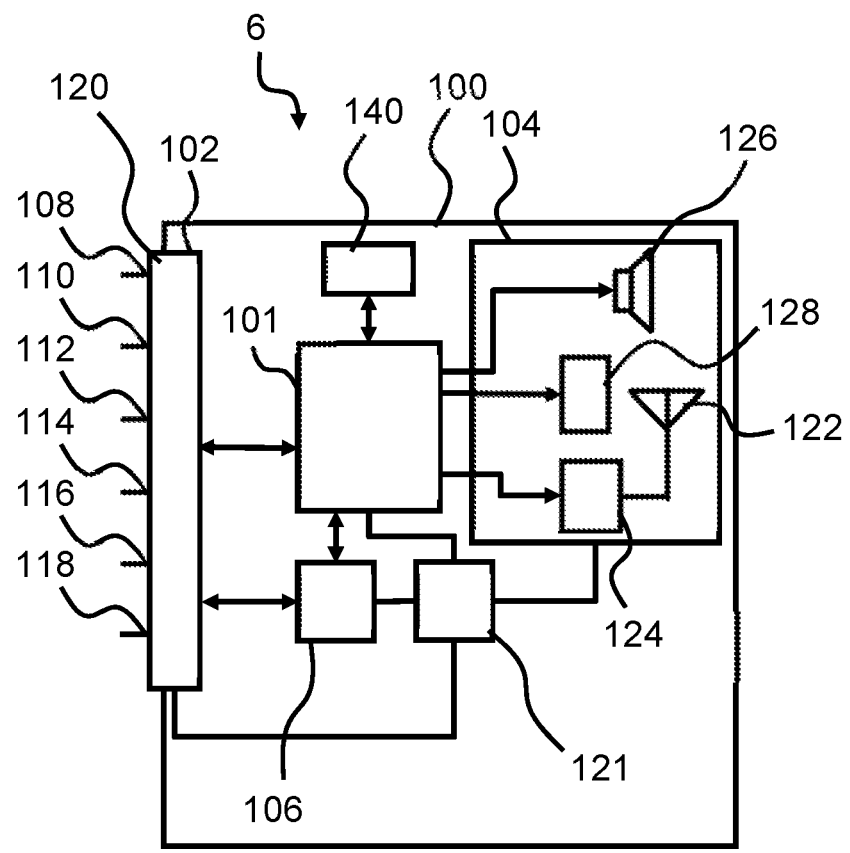
FIG. 8 is a schematic block diagram of an exemplary monitor device.

FIG. 8 is a schematic block diagram of an exemplary monitor device 6. The monitor device 6 may comprise a monitor device housing 100, a processor 101 and one or more interfaces. The one or more interfaces may include a first interface 102 and/or a second interface 104. The monitor device 6 may comprises a memory 106 for storing ostomy data and/or parameter data based on the ostomy data. The memory 106 may be connected to the processor 101 and/or the first interface 102.

The first interface 102 may be configured as an appliance interface for electrically and/or mechanically connecting the monitor device 6 to the sensor patch, as described with respect to previous figures. The first interface 102 may comprise a plurality of terminals for forming electrical connections with respective terminals of the sensor patch. The first interface 102 may comprise a ground terminal 108, a first terminal 110, a second terminal 112 and a third terminal 114. The first interface 102 optionally comprises a fourth terminal 116 and a fifth terminal 118. The first interface 102 of the monitor device 6 may comprise a coupling part 120 for forming a mechanical connection, such as a releasable coupling between the monitor device and the sensor patch.

The monitor device 6 may comprise a power unit 121 for powering the monitor device and active components thereof, i.e. the power unit 121 may be connected to the processor 101, the first interface 102, the second interface 104, and/or the memory 106. The power unit may comprise a battery and charging circuitry.

The second interface 104 of monitor device may be configured as an accessory interface for connecting the monitor device 6 to one or more accessory devices, such as a mobile phone or another suitable accessory device. The second interface 104 may comprise an antenna 122 and a wireless transceiver 124, e.g. configured for wireless communication with accessory device(s). Optionally, the second interface 104 comprises a loudspeaker 126 and/or a haptic feedback element 128 for provision of respective audio signal and/or haptic feedback to the user.

The monitor device 6 may comprise a sensor unit 140 connected to the processor 101. The sensor unit 140 may comprise a temperature sensor for feeding temperature data to the processor and a G-sensor or accelerometer for feeding acceleration data to the processor 101.

The monitor device 6, such as the processor 101 of the monitor device, may be configured to evaluate attachment of a sensor patch to a base plate. For example, the monitor device 6, such as the processor 101 of the monitor device, may be configured to perform the method and/or part of the method as described with respect to FIG. 7.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A method for evaluating attachment of a sensor patch to a base plate for an ostomy appliance, the method comprising:
    measuring one or more characteristic quantities of the sensor patch, the one or more characteristic quantities comprising a first characteristic quantity indicative of electrical capacitance between a first electrode and a second electrode of the sensor patch, wherein the base plate comprises:
        at least a first layer of an adhesive material adapted for attachment of the base plate to the skin surface of a user;
        a backing layer comprising a film material and having a distal surface and a proximal surface; and
        a centre portion surrounding a stoma-receiving opening extending through the base plate,
    and wherein the sensor patch is adapted for attachment to the first layer of the base plate, and wherein the sensor patch comprises:
        a sensor assembly comprising a plurality of electrodes including the first electrode and the second electrode for forming a first sensor; and
    determining whether the one or more characteristic quantities satisfies one or more attachment criteria.

2. The method according to claim 1, wherein determining whether the one or more characteristic quantities satisfies the one or more attachment criteria comprises comparing the first characteristic quantity and a first characteristic threshold value.

3. The method according to claim 2, wherein the one or more characteristic quantities satisfying the one or more attachment criteria requires that the first characteristic quantity is above the first characteristic threshold value.

4. The method according to claim 2, wherein the one or more characteristic quantities satisfying the one or more attachment criteria requires that the first characteristic quantity is below the first characteristic threshold value.

5. The method according to claim 1, wherein the one or more characteristic quantities includes a second characteristic quantity being indicative of electrical resistance between the first electrode and the second electrode.

6. The method according to claim 5, wherein determining whether the one or more characteristic quantities satisfies the one or more attachment criteria comprises comparing the second characteristic quantity and a second characteristic threshold value.

7. The method according to claim 6, wherein the one or more characteristic quantities satisfies the one or more attachment criteria if the second characteristic quantity is above the second characteristic threshold value.

8. The method according to claim 6, wherein the one or more characteristic quantities satisfies the one or more attachment criteria if the second characteristic quantity is below the second characteristic threshold value.

9. The method according to claim 5, wherein the one or more characteristic quantities includes a first characteristic quantity being indicative of electrical capacitance between the first electrode and the second electrode and wherein determining whether the one or more characteristic quantities satisfies the one or more attachment criteria comprise comparing a third characteristic quantity and a third characteristic threshold value, wherein the third characteristic quantity is based on the first characteristic quantity and the second characteristic quantity.

10. The method according to claim 9, wherein the one or more characteristic quantities satisfies the one or more attachment criteria if the third characteristic quantity is above the third characteristic threshold value.

11. The method according to claim 9, wherein the one or more characteristic quantities satisfies the one or more attachment criteria if the third characteristic quantity is below the third characteristic threshold value.

12. The method according to claim 1, comprising in accordance with the one or more characteristic quantities not satisfying the one or more attachment criteria, issuing a failure signal indicative of the sensor patch not being sufficiently attached.

13. The method according to claim 1, comprising in accordance with the one or more characteristic quantities satisfying the one or more attachment criteria, issuing a success signal indicative of the sensor patch being sufficiently attached.

14. The method according to claim 1, wherein measuring the one or more characteristic quantities and determining whether the one or more characteristic quantities satisfies the one or more attachment criteria is performed prior to attachment of the base plate to the skin of the user.

15. The method according to claim 1, wherein the sensor patch comprises a monitor interface configured for connecting the sensor assembly to a monitor device, and wherein the method comprises connecting the monitor device to the sensor assembly prior to measuring the one or more characteristic quantities.

16. The method according to claim 15, wherein measuring the one or more characteristic quantities and determining whether the one or more characteristic quantities satisfies the one or more attachment criteria is performed by the monitor device.

17. The method according to claim 15, wherein when the one or more characteristic quantities do not satisfy the one or more attachment criteria, issuing a failure signal indicative of the sensor patch not being sufficiently attached, wherein issuing the failure signal is performed by the monitor device.

18. The method according to claim 15, wherein when the one or more characteristic quantities do not satisfy the one or more attachment criteria, issuing a failure signal indicative of the sensor patch not being sufficiently attached, wherein issuing the failure signal is performed by an auxiliary device coupled to the monitor device.

19. The method according to claim 15, wherein when the one or more characteristic quantities satisfies the one or more attachment criteria, issuing a success signal indicative of the sensor patch being sufficiently attached, wherein issuing the success signal is performed by the monitor device.

20. The method according to claim 14, wherein when the one or more characteristic quantities satisfies the one or more attachment criteria, issuing a success signal indicative of the sensor patch being sufficiently attached, wherein issuing the success signal is performed by an auxiliary device coupled to the monitor device.

21. The method according to claim 1, wherein the sensor patch comprises an adhesive sensor layer arranged on a proximal side of the sensor assembly.

22. The method according to claim 1, wherein the sensor patch comprises a shielding layer of an electrically conductive material, the shielding layer being arranged on a distal side of the sensor assembly.

23. A method for evaluating attachment of a sensor patch to a base plate for an ostomy appliance, the method comprising:
   measuring an electrical characteristic between a first electrode and a second electrode of the sensor patch, wherein:
      the sensor patch is adapted for attachment to an adhesive layer of the base plate; and
      the sensor patch comprises a sensor assembly comprising a plurality of electrodes including the first electrode and the second electrode for forming a first sensor; and
   determining whether the electrical characteristic of the sensor patch satisfies a threshold of an attachment criteria, wherein the sensor patch is determined to be sufficiently attached to the base plate when the electrical characteristic of the sensor patch exceeds the threshold.

* * * * *